United States Patent [19]
Yamamoto et al.

[11] Patent Number: 6,066,727
[45] Date of Patent: May 23, 2000

[54] ORGANOPOLYSILOXANE-GRAFTED POLYSACCHARIDE COMPOUND

[75] Inventors: Akira Yamamoto; Ichiro Ono, both of Gunma-ken, Japan

[73] Assignee: Shin-Etsu Chemical Co., Ltd., Tokyo, Japan

[21] Appl. No.: 09/325,797

[22] Filed: Jun. 4, 1999

[30] Foreign Application Priority Data

Jun. 5, 1998 [JP] Japan ................... 10-157735

[51] Int. Cl.$^7$ ...................................... C07H 1/00
[52] U.S. Cl. .................... 536/124; 536/17.1; 536/120; 536/123.1; 556/443
[58] Field of Search ................ 536/4.1, 17.1, 536/124, 120, 123.1; 556/465, 466, 482, 443

[56] References Cited

U.S. PATENT DOCUMENTS 5,583,244 12/1996 Uchida et al. ..................... 556/419
5,831,080 11/1998 Sejpka et al. ..................... 536/124

*Primary Examiner*—Elli Peselev
*Attorney, Agent, or Firm*—Millen, White, Zelano & Branigan, P.C.

[57] ABSTRACT

Disclosed is a novel method for the preparation of an organo-polysiloxane-grafted polysaccharide compound which is particularly useful as an additive ingredient in various types of cosmetic and toiletry preparations. The method utilizes a reaction between epoxy groups of a diorganopolysiloxane, e.g., dimethylpolysiloxane, terminated at a single molecular chain end with a 2-(3,4-epoxycyclohexyl)ethyl group and carboxyl groups in a carboxyl group-containing polysaccharide compound such as hydroxypropyl methyl cellulose phthalate and hydroxypropyl methyl cellulose acetate succinate dissolved in an organic solvent. The reaction proceeds efficiently without addition of any catalytic compounds almost quantitatively under moderate reaction conditions.

11 Claims, No Drawings

ORGANOPOLYSILOXANE-GRAFTED POLYSACCHARIDE COMPOUND

BACKGROUND OF THE INVENTION

The present invention relates to an organopolysiloxane-grafted polysaccharide compound or, more particularly, to a novel and efficient method for the preparation of an organopolysiloxane-grafted polysaccharide compound such as a cellulose derivative substituted by a grafting moiety of an organopolysiloxane, which is useful as an additive ingredient in various kinds of cosmetic and toiletry preparations.

It is known in the prior art that organopolysiloxane-grafted polysaccharide compounds have usefulness not only as a film-forming additive ingredient in hair-care and skin-care toiletry and cosmetic preparations but also as a material of a membrane for gas separation, back-coating agent on thermographic printing paper sheets and an additive in coating compositions such as paints.

Several different methods are proposed for the preparation of an organopolysiloxane-grafted polysaccharide compound in, for example, Japanese Patent Publications 64-8001 and 64-11202, Japanese Patents 071051 and 071084 and Japanese Patent Kokai 7-70204 and 9-136901. These prior art methods, however, are economically not quite satisfactory as an industrial process because of the low efficiency of the reaction between a polysaccharide derivative and an organopolysiloxane as the polymeric reactants pertaining to the grafting reaction even by the use of a catalyst due to the so large difference in the nature of the respective reactants necessarily resulting in a low yield of the desired graft polymer product which contains an unduly large amount of the unreacted reactants. More disadvantageously, the reaction product containing the unreacted reactants and the catalyst compound as such usually cannot be used as an additive ingredient in a cosmetic or toiletry preparation unless the unreacted matters and the catalyst compound are removed in a very complicated and hence expensive purification procedure involving thorough washing of the reaction product with an organic solvent, recovering and recycling of the organic solvent and drying of the reaction product.

SUMMARY OF THE INVENTION

In view of the above described problems in the conventional methods for the preparation of an organopolysiloxane-grafted polysaccharide compound, the present invention has an object to provide a novel and efficient method capable of giving an organopolysiloxane-grafted polysaccharide compound in a high yield even without using any catalyst, the product containing little amount of unreacted matters and absolutely no catalyst compound so as to be useful as an additive ingredient in cosmetic and toiletry preparations without undertaking any purification processes.

Thus, the method of the present invention for the preparation of an organopolysiloxane-grafted polysaccharide compound comprises the steps of:

(a) dissolving, in an organic solvent, a polysaccharide compound having carboxyl groups in the molecule and an epoxy-terminated organopolysiloxane compound represented by the general formula

in which the subscript n is a positive integer in the range from 3 to 200, each R is, independently from the others, a monovalent hydrocarbon group or a halogen-substituted monovalent hydrocarbon group and Ep is a 2-(3,4-epoxycyclohexyl)ethyl group, in such a proportion that, preferably, the amount of the epoxy-terminated organopolysiloxane compound does not exceed a stoichiometrically equimolar amount to the carboxyl groups in the polysaccharide compound to give a uniform solution; and (b) heating the solution at a temperature in the range from 60 to 200° C. to effect a reaction between the carboxyl groups in the polysaccharide compound and the epoxy groups in the organopolysiloxane compound.

DETAILED DESCRIPTION OF THE PREFERRED EMBODIMENTS

As is described above, the inventive method comprises a reaction between a carboxyl group-containing polysaccharide compound and an epoxy-terminated organopolysiloxane compound in an organic solvent and, quite unexpectedly, the reaction therebetween proceeds almost quantitatively at a moderate rate even in the absence of any catalytic compound so that, when the starting reaction mixture is prepared by using the epoxy-terminated organopolysiloxane in an amount not exceeding equimolar to the carboxyl groups in the carboxyl group-containing polysaccharide compound, the resultant reaction product contains no or little amount of the unreacted orgariopolysiloxane compound enabling use of the reaction product by omitting or greatly simplifying the expensive purification procedure necessitated in the prior art methods for the removal of the unreacted organopolysiloxane compound and catalytic compound. When the reaction is conducted with an excess molar amount of the carboxyl groups in the polysaccharide compound over equimolar to the epoxy groups in the organopolysiloxane compound, the reaction product can contain a substantial amount of the carboxyl groups unreacted so as to exhibit the advantages by the carboxyl groups and the organopolysiloxane grafts in combination.

Step (a) of the inventive method is for the preparation of a solution as a reaction mixture containing the carboxyl group-containing polysaccharide compound and the epoxy-terminated organopolysiloxane compound jointly dissolved in an organic solvent. Accordingly, the carboxyl group-containing polysaccharide compound must be soluble in at least one organic solvent which also dissolves the epoxy-terminated organopolysiloxane compound. Several classes of semi-synthetic polysaccharide derivatives are known to meet these requirements including hydroxypropyl methyl cellulose phtihalate, hydroxypropyl methyl cellulose acetate succinate, carboxymethyl ethyl cellulose, pullulan acetate phthalate and the like and they can be selected depending on the particular properties desired of the product, though not particularly limitative thereto. Among the above named carboxyl group-containing polysaccharide compounds, it is advantageous, if the purpose of the product can be met with, to use a hydroxypropyl methyl cellulose phthalate or hydroxypropyl methyl cellulose acetate succinate as the reactant to be grafted because of the good commercial availability and inexpensiveness of these cellulose derivatives commercialized as an enterosoluble coating agent on solid medicaments.

The epoxy-terminated organopolysiloxane compound as the other reactant in the inventive method is represented by the above given general formula (I). In the formula, each R is, independently from the others, a monovalent hydrocarbon group having 1 to 10 carbon atoms exemplified by alkyl groups such as methyl, ethyl, propyl and butyl groups, cycloalkyl groups such as cyclopentyl and cyclohexyl groups, aryl groups such as phenyl and tolyl groups, aralkyl groups such as benzyl and phenethyl groups and alkenyl groups such as vinyl and allyl groups. These monovalent hydrocarbon groups can optionally be partially or fully substituted by halogen atoms or, in particular, fluorine atoms as in chloromethyl and 3,3,3-trifluoropropyl groups. It is advantageous in most cases that all or at least 90 mole % of the groups denoted by R are methyl groups, the balance, if any, being phenyl and/or vinyl groups. The group denoted by Ep at one of the molecular chain ends of the organopolysiloxane in the general formula (I) is a 2-(3,4-epoxycyclohexyl)ethyl group. The subscript n in the general formula (I) is a positive integer of 3 to 200. When n is smaller than 3, the grafted polysaccharide compound can hardly exhibit the advantageous properties as a silicone-grafted product while, when n is too large, the reactivity of the terminal epoxy groups with the carboxyl groups is unduly decreased not to give a practically feasible reaction rate.

The epoxy-terminated organopolysiloxane compound described above as a reactant in the inventive method is obtained by the hydrosilation reaction between an organopolysiloxane terminated at one molecular chain end with a silicon-bonded hydrogen atom as represented by the general formula

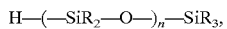

In which R and n each have the same meaning as defined before, and 1-vinyl-3,4-epoxycyclohexane in the presence of a platinum catalyst.

The reaction mixture in the inventive method is prepared by dissolving the above described carboxyl group-containing polysaccharide compound and the epoxy-terminated organopolysiloxane compound in an organic solvent which, naturally, must have a dissolving power to both of the two reactants in combination. Suitable organic solvents can be selected from ketone solvents such as acetone and cyclohexanone, ether solvents such as dioxane and ester solvents such as ethyleneglycol monobutyl ether acetate, which can be used either singly or as a mixture of two kinds or more according to need. As is mentioned before, it is usually advantageous that the two reactants are dissolved in the organic solvent in such a proportion that the amount of the epoxy-terminated organopolysiloxane does not exceed equimolar to the carboxyl groups in the carboxyl group-containing polysaccharide compound. The concentration of the reaction mixture relative to the carboxyl group-containing polysaccharide compound should preferably be in the range from 50 to 500 g/liter though not particularly limitative thereto. The amount or concentration of the epoxy-terminated organopolysiloxane compound naturally depends on the desired degree of grafting modification of the polysaccharide compound.

In step (b) of the inventive method, the solution of the reactants as a reaction mixture prepared in the above described manner is heated under agitation at a temperature in the range from 60 to 200° C. under reflux or, if necessary, under pressurization in an atmosphere of an inert gas so that the reaction between the carboxyl groups of the polysaccharide compound and the epoxy groups of the organopolysiloxane compound proceeds. The reaction is usually complete to quantitatively give the organopolysiloxane-grafted polysaccharide compound by heating the reaction mixture for several hours or for at least one hour, though dependent on the reaction temperature and other factors affecting the reaction rate.

The organopolysiloxane-grafted polysaccharide compound as the product of the inventive method can be isolated from the reaction mixture after completion of the reaction as precipitates by the addition of another organic solvent having poor dissolving power to the grafted polysaccharide compound such as n-hexane followed by drying. It is, however, sometimes the case that, by virtue of the very low content of unreacted matters and absence of any catalytic compounds in the reaction mixture, the reaction mixture in the form of a solution of the product is used as such or merely after replacement of the solvent with another solvent suitable for the intended application.

As is mentioned before, the most promising application of the organopolysiloxane-grafted polysaccharide compound is as an additive ingredient in a hair-care or skin-care toiletry preparation. Since the degree of grafting modification of the polysaccharide compound is controllable to leave a specified amount of unreacted carboxyl groups in the starting polysaccharide compound, a hair-care treatment composition compounded with the organopolysiloxane-grafted polysaccharide compound prepared by the inventive method can be imparted with the advantages inherent in both of the organopolysiloxane and the carboxyl group-containing polysaccharide compound. For example, the hair treated with the hair-care treatment preparation is imparted with combing smoothness and non-sticky touch feeling as an inherence of an organopolysiloxane component and with good removability after treatment by using a conventional detergent or cleansing composition as an inherence of the other component. Besides, the hair-care treatment preparation imparts improvements relative to water repellency, lubricity, glossiness and film formation to the hair treated therewith. Needless to say, toiletry preparations compounded with the product of the inventive method are free from the problems relative to safety against human health.

The organopolysiloxane-grafted polysaccharide compound obtained by the inventive method, referred to as the inventive product hereinafter, can be compounded with other base ingredients of toiletry preparations either as such or in the form of a solution in an appropriate organic solvent. Most of the base ingredients of conventional toiletry preparations have compatibility with the inventive product including waxes, oiling agents, powder materials, metal soaps, gelation agents, tar dyes, surface active agents, polyhydric alcohols, polymeric compounds, water, organic solvents, antiseptic agents, ultraviolet absorbers, antioxidants and others. The toiletry preparations include a variety of preparation forms such as hair-care treatment compositions, cosmetic base preparations, makeup cosmetic compositions and others depending on the particular object of the toiletry and cosmetic preparations. The compounding amount of the inventive product in a cosmetic or toiletry preparation may widely differ depending on the form of the preparations and the particular intention of the formulation but is in the range of, usually, from 1 to 50% by weight or, in most cases, from 3 to 30% by weight. When the compounding amount thereof is too small, the desired effects of improvements cannot be fully obtained as a matter of course while, when the amount thereof is too large, an undue increase results in the viscosity or consistency of the toiletry preparation to cause difficulties in the compounding works and in the use of the toiletry preparations.

In the following, the method of the present invention is described in more detail by way of Examples, which, however, never limit the scope of the invention in any way.

EXAMPLE 1

Into a glass flask equipped with a stirrer, thermometer and reflux condenser were introduced a hydroxypropyl methyl cellulose phthalate containing 33.4% by weight of carboxybenzoyl groups (a product by Shin-Etsu Chemical Co., HP-55) in an amount of 75 g corresponding to 168.2 mmoles of the carboxyl groups and an epoxy-modified dimethylpolysiloxane, of which the epoxy equivalent was 2270 g/mole, expressed by the formula

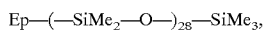
Ep—(—SiMe$_2$—O—)$_{28}$—SiMe$_3$, in which Me is a methyl group and Ep is a 2-(3,4-epoxycyclohexyl)ethyl group, in an amount of 25 g corresponding to 11.0 mmoles of the epoxy groups together with 400 g of cyclohexanone under agitation to give a uniform solution, which was heated and agitated at 150° C. for 5 hours under a stream of nitrogem gas to obtain a light yellow, slightly cloudy liquid. After cooling to 30° C., this liquid was admixed under agitation with 1000 ml of n-hexane to precipitate the polymeric material which was collected by filtration and dried at 100° C. for 3 hours under reduced pressure to give 92 g of a light yellow powder, referred to as the Product-1 hereinafter.

This powder product was subjected to infrared absorption spectrophotometric analysis to detect, besides the characteristic absorption bands assignable to the chemical bonds in the hydroxypropyl methyl cellulose phthalate, several absorption bands due to the dimethylpolysiloxane moiety having wave numbers including 1262 cm$^{-1}$ assignable to Si—Me, 1071 and 1123 cm$^{-1}$ assignable to Si—O—Si and 801 cm$^{-1}$ assignable to Me$_2$—Si—O.

Further, the Product-1 was subjected to quantitative determination of the carboxybenzoyl groups according to the assay procedure specified in Japanese Pharmacopoeia for hydroxypropyl methyl cellulose phthalate to find a value of 23.5% indicating that the reaction of the carboxyl groups and the epoxy groups in the respective reactants was substantially quantitative.

EXAMPLE 2

The procedure for the preparation of another dimethylpolysiloxane-grafted polysaccharide compound, referred to as the Product-2 hereinafter, was substantially the same as in Example 1 excepting for the replacement of the hydroxypropyl methyl cellulose phthalate with a hydroxypropyl methyl cellulose acetate succinate, of which the content of the succinoyl groups was 15.6% (a product by Shin-Etsu Chemical Co., AS-LG) in the same amount corresponding to a content of the carboxyl groups of 115.6 mmoles to obtain 93 g of a light yellow powder product.

This powder product was subjected to infrared absorption spectrophotometric analysis to detect, besides the characteristic absorption bands assignable to the chemical bonds in the hydroxypropyl methyl cellulose acetate succinate, several absorption bands due to the dimethylpolysiloxane moiety having wave numbers including 1238 cm$^{-1}$ assignable to Si—Me, 1057 and 1122 cm$^{-1}$ assignable to Si—O—Si and 803 cm$^{-1}$ assignable to Me$_2$—Si—O. Further, this Product-2 was subjected to quantitative determination of the succinoyl groups to find a value of 10.8% indicating that the reaction of the carboxyl groups and the epoxy groups in the respective reactants was substantially quantitative.

APPLICATION EXAMPLE

Two mousse compositions for hair treatment were prepared according to the following formulation given in % by weight from the ingredients including the Product-1 or Product-2 prepared in Example 1 and Example 2, respectively.

| | |
|---|---|
| (1) Product-1 or -2 | 5.0% |
| (2) Liquid paraffin | 5.0% |
| (3) Polyoxyethylene hydrogenated castor oil | 1.0% |
| (4) Perfume | q.s. |
| (5) Deionized water | (balance to 100%) |
| (6) Ethanol | 15.0% |
| (7) Liquefied petroleum gas | 8.0% |

A further mousse composition was prepared in the same formulation as above for comparative purpose excepting for the replacement of the Product-1 or Product-2 with the same amount of the ungrafted hydroxypropyl methyl cellulose phthalate (HP-55, see Example 1).

These three mousse compositions were subjected to comparative organoleptic evaluation tests of hair treatment to obtain results that the mousse compositions formulated with the Product-1 and -2 were apparently superior to the comparative composition in the testing items of absence of stickiness on the treated hail, lubricity of the hair and combing smoothness and were about equivalent to the comparative composition in respect of hair setting and removability by cleansing leading to an overall conclusion that the composition compounded with the inventive product were generally more acceptable than the comparative composition.

What is claimed is:

1. A method for the preparation of an organopolysiloxane-grafted polysaccharide compound which comprises the steps of:

(a) dissolving, in an organic solvent, a polysaccharide compound having carboxyl groups in the molecule and an epoxy-terminated organopolysiloxane compound represented by the formula

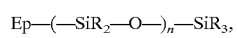
   Ep—(—SiR$_2$—O—)$_n$—SiR$_3$, in which the subscript n is a positive integer in the range from 3 to 200, each R is, independently from the others, a monovalent hydrocarbon group or a halogen-substituted monovalent hydrocarbon group and Ep is a 2-(3,4-epoxycyclohexyl)ethyl group, to give a uniform solution; and (b) heating the solution at a temperature in the range from 60 to 200° C. to effect a reaction between the carboxyl groups in the polysaccharide compound and the epoxy groups in the organopolysiloxane compound.

2. The method for the preparation of an organopolysiloxane-grafted polysaccharide compound as claimed in claim 1 in which the amount of the epoxy-terminated organopolysiloxane compound does not exceed a stoichiometrically equimolar amount to the carboxyl groups in the polysaccharide compound.

3. The method for the preparation of an organopolysiloxane-grafted polysaccharide compound as claimed in claim 1 in which the polysaccharide compound having carboxyl groups in the molecule is a hydroxypropyl methyl cellulose phthalate or hydroxypropyl methyl cellulose acetate succinate.

4. The method for the preparation of an organopolysiloxane-grafted polysaccharide compound as claimed in claim 1 in which the organic solvent is selected from the group consisting of ketones, ethers and esters.

5. The method for the preparation of an organopolysiloxane-grafted polysaccharide compound as claimed in claim 1 in which at least 90 mole % of the monovalent hydrocarbon groups denoted by R are methyl groups.

6. The method for the preparation of an organopolysiloxane-grafted polysaccharide compound as claimed in claim 1 in which heating of the solution in step (b) is performed for at least 1 hour.

7. The method for the preparation of an organopolysiloxane-grafted polysaccharide compound as claimed in claim 1 in which the solution prepared in step (a) contains the polysaccharide compound in a concentration in the range from 50 to 500 g/liter.

8. The method of claim 1, wherein the reaction between the carboxyl groups in the polysaccharide compound and the epoxy groups in the organopolysiloxane compound is conducted in the absence of a catalyst.

9. The method of claim 1, wherein the amount of the epoxy-terminated organopolysiloxane compound exceeds a stoichiometrically equimolar amount of the carboxyl groups in the polysaccharide compound.

10. The method of claim 1, wherein in the epoxy-terminated organopolysiloxane compound the R groups are independently selected from the group consisting of alkyl, alkenyl, cycloalkyl, phenyl, tolyl, benzyl or phenethyl groups optionally substituted with halogen atoms.

11. The method of claim 1, wherein the reaction in step (b) is conducted under pressurization of an inert gas atmosphere.

* * * * *